United States Patent
Vatanparvar et al.

(10) Patent No.: US 11,890,078 B2
(45) Date of Patent: Feb. 6, 2024

(54) SYSTEM AND METHOD FOR CONDUCTING ON-DEVICE SPIROMETRY TEST

(71) Applicant: Samsung Electronics Co., Ltd., Suwon-si (KR)

(72) Inventors: Korosh Vatanparvar, Santa Clara, CA (US); Viswam Nathan, Mountain View, CA (US); Md Mahbubur Rahman, San Jose, CA (US); Ebrahim Nematihosseinabadi, Santa Clara, CA (US); Jilong Kuang, San Jose, CA (US); Jun (Alex) Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 784 days.

(21) Appl. No.: 16/786,801

(22) Filed: Feb. 10, 2020

(65) Prior Publication Data

US 2021/0244314 A1    Aug. 12, 2021

(51) Int. Cl.
| | |
|---|---|
| *A61B 5/00* | (2006.01) |
| *A61B 5/091* | (2006.01) |
| *A61B 5/087* | (2006.01) |
| *G06V 10/80* | (2022.01) |
| *G06V 40/16* | (2022.01) |

(52) U.S. Cl.
CPC .......... *A61B 5/0077* (2013.01); *A61B 5/0871* (2013.01); *A61B 5/091* (2013.01); *A61B 5/486* (2013.01); *A61B 5/7221* (2013.01); *G06V 10/803* (2022.01); *G06V 40/171* (2022.01); *A61B 2562/0204* (2013.01)

(58) Field of Classification Search
CPC ..... A61B 5/091; A61B 5/0077; A61B 5/0871; A61B 5/486; A61B 5/7221; A61B 2562/0204
See application file for complete search history.

(56) References Cited

U.S. PATENT DOCUMENTS

| | | | |
|---|---|---|---|
| 7,447,333 B1 * | 11/2008 | Masticola | G16H 50/80 382/128 |
| 9,993,193 B2 | 6/2018 | Van Vugt et al. | |
| 10,028,675 B2 * | 7/2018 | Patel | A61B 5/091 |
| 2012/0041279 A1 * | 2/2012 | Freeman | A61M 5/14276 600/534 |

(Continued)

FOREIGN PATENT DOCUMENTS

| | | | |
|---|---|---|---|
| CN | 105286869 A | * | 2/2016 |
| CN | 108968962 A | | 12/2018 |

(Continued)

*Primary Examiner* — Joel Lamprecht
*Assistant Examiner* — Helene Bor (57) ABSTRACT

A method includes receiving, by an electronic device, sensor data during a spirometry test of a user, the sensor data comprising audio data of the user and distance data of a distance from a face of the user to the electronic device. The method also includes obtaining, by the electronic device, an amount of air volume exchange and at least one pulmonary health parameter that are determined based on the audio data and the distance data. The method also includes presenting an indicator on a display of the electronic device for use by the user or a medical provider, the indicator representing the amount of air volume exchange.

20 Claims, 7 Drawing Sheets

(56) References Cited

U.S. PATENT DOCUMENTS

| | | | |
|---|---|---|---|
| 2013/0079658 A1* | 3/2013 | Cardoso | G01N 33/497 600/532 |
| 2013/0184540 A1* | 7/2013 | Boschetti Sacco | A61B 5/4884 600/301 |
| 2015/0126888 A1* | 5/2015 | Patel | G16H 50/30 600/538 |
| 2015/0265187 A1* | 9/2015 | Bernal | A61B 5/1128 600/534 |
| 2017/0273597 A1* | 9/2017 | Schuelke | A61B 5/0022 |
| 2018/0092595 A1 | 4/2018 | Chen et al. | |

FOREIGN PATENT DOCUMENTS

| | | | | |
|---|---|---|---|---|
| JP | 4557059 B2 | 10/2010 | | |
| WO | WO-2017136639 A1 * | 8/2017 | | A61B 5/0002 |
| WO | 2018/170009 A1 | 9/2018 | | |

* cited by examiner

SYSTEM AND METHOD FOR CONDUCTING ON-DEVICE SPIROMETRY TEST

TECHNICAL FIELD

This disclosure relates generally to health monitoring systems and methods. More specifically, this disclosure relates to a system and method for conducting an on-device, effort-aware spirometry test.

BACKGROUND

Chronic respiratory diseases (chronic diseases of the airways) currently affect an estimated 40 million people in the United States alone and are the third leading cause of death. Common respiratory diseases include asthma, chronic obstructive pulmonary disease (COPD), occupational lung disease, and chronic bronchitis. These diseases can cause increased inflammation and mucus in the lungs, narrow or swollen airways, and partial blocking of airflow. One test that is commonly used in diagnosis and treatment of chronic respiratory diseases is spirometry. Spirometry is a pulmonary function test that can be used to diagnose breathing conditions, periodically monitor lung conditions, determine whether medications are working, and reduce chronic respiratory morbidity.

SUMMARY

This disclosure provides a system and method for conducting an on-device, effort-aware spirometry test.

In a first embodiment, a method includes receiving, by an electronic device, sensor data during a spirometry test of a user, the sensor data comprising audio data of the user and distance data of a distance from a face of the user to the electronic device. The method also includes obtaining, by the electronic device, an amount of air volume exchange and at least one pulmonary health parameter that are determined based on the audio data and the distance data. The method also includes presenting an indicator on a display of the electronic device for use by the user or a medical provider, the indicator representing the amount of air volume exchange.

In a second embodiment, an electronic device includes at least one sensor, a processor, and a display. The processor is configured to receive sensor data obtained by the at least one sensor during a spirometry test of a user, the sensor data comprising audio data of the user and distance data of a distance from a face of the user to the electronic device; and obtain an amount of air volume exchange and at least one pulmonary health parameter that are determined based on the audio data and the distance data. The display is configured to present an indicator for use by the user or a medical provider, the indicator representing the amount of air volume exchange.

In a third embodiment, a non-transitory computer readable medium contains computer readable program code that, when executed, causes at least one processor of an electronic device to receive sensor data during a spirometry test of a user, the sensor data comprising audio data of the user and distance data of a distance from a face of the user to the electronic device; obtain an amount of air volume exchange and at least one pulmonary health parameter that are determined based on the audio data and the distance data; and present an indicator on a display of the electronic device for use by the user or a medical provider, the indicator representing the amount of air volume exchange.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B.

As used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smart phone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic appcessory, an electronic tattoo, a smart mirror, or a smart watch). Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such SAMSUNG HOMESYNC, APPLETV, or GOOGLE TV), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

The figures discussed below and the various embodiments used to describe the principles of this disclosure in this patent document are by way of illustration only and should not be construed in any way to limit the scope of the disclosure. Those skilled in the art will understand that the principles of this disclosure can be implemented in any suitably arranged system.

It is estimated that 235 million people in the world suffer from asthma, and that more than 250 million people have Chronic Obstructive Pulmonary Disease (COPD). Asthma is a condition in which the person's airways narrow and swell and produce extra mucus. This can make breathing difficult and trigger coughing, wheezing and shortness of breath. COPD is an umbrella term used to describe progressive lung diseases including emphysema, chronic bronchitis, pulmonary fibrosis, and refractory (non-reversible) asthma. These diseases are mainly characterized by increasing breathlessness.

Many asthma attacks have the potential to be life-threatening. Fatal asthma can occur in anyone with mild intermittent to more severe asthma. COPD is the third leading cause of death by disease in the United States; COPD also can cause serious long-term disability and early death. At the present time there is no cure, and the number of people dying from COPD is growing. However, in many cases, these diseases can be found early, and much can be done to treat and help manage the diseases.

Spirometry is used to diagnose conditions that affect breathing such as asthma and COPD. Moreover, spirometry may be used periodically to monitor a person's lung condition and check whether a treatment for a chronic lung condition is helping the person breathe better. Regular tracking of a patient's pulmonary function and health condition is important to prevent any significant lung deterioration or severe exacerbation, especially for already-diagnosed pulmonary patients. Spirometry may also be used periodically to check how well a patient's medications are working and whether the patient's breathing problems are under control. There is some evidence that application of spirometry testing in general practice may reduce the number of undetected cases with chronic respiratory morbidity as well as diagnostic misclassification, which may lead to overall improved respiratory health.

There is a correlation between a person's lung function and capacity and their overall physical endurance and health. For instance, athletes have larger lung capacity and higher expiratory air flow compared to non-athlete healthy people. Therefore, spirometry has been also utilized by general population and athletes as well, to evaluate and monitor their ventilatory function, lung capacity, and physical endurance regularly. With an increasing population regularly engaged in sports and exercise, this information can be utilized to provide feedback and adjust their daily physical or sports activity.

Current spirometry tests are typically performed in a medical office using dedicated, medical grade equipment. The subjects are required to blow into a device as hard as possible in order to measure the air flow and volume figures. In-office spirometry tests can require frequent clinic visits by the patient, which can be costly and inconvenient, especially for maintaining a regular tracking of their lung function. Such in-office tests also can require expensive medical equipment and must be attended by a medical professional to ensure that the test is performed correctly. Despite the presence of a medical professional, some tests are incorrectly performed and generate suboptimal results, such as when the patient does not exhale forcefully enough or for long enough.

Recently, FDA-approved portable devices have become available which can provide some of the same functionality of the in-clinic medical devices. Patients are able to use these devices in their home and conduct the spirometry test on their own. However, the limited availability and high cost of these devices still pose challenges for some patients to utilize them on a daily basis. Moreover, as the test is an intrinsically challenging task, many patients cannot always correctly perform the test without sufficient pre-training, thereby failing the test or getting inaccurate results. For example, the distance between the device and the patient and the openness of the patient's mouth can influence the audio features and thereby the test results.

To address these and other issues, embodiments of this disclosure provide systems and methods for a portable spirometry test that can be performed conveniently at any time and in any location using a smart phone or a wearable device such as a smart watch. For example, a patient can use their own device and conduct the spirometry test at their home. In some embodiments, the patient conducts the spirometry test while holding the device as they would do in a medical setting. The patient deeply inhales and forcefully exhales facing the camera and microphone of the device. The device then records audio captured by the microphone, mouth and face images captured by one or more cameras, and measured distance of the patient's face from the device. The combination of image, audio, and distance from the patient's face can be used to compensate for different subject variations (e.g., face/mouth structure, distance, etc.) encountered while taking the test. Moreover, the extracted data enables the device to quantify the effort of the patient during the test, compare to their maximum baseline, and validate the correctness of the test. Therefore, while performing the test, the patient can be guided using visual, audio, or haptic feedback to help them correctly accomplish the test.

Figure 1:
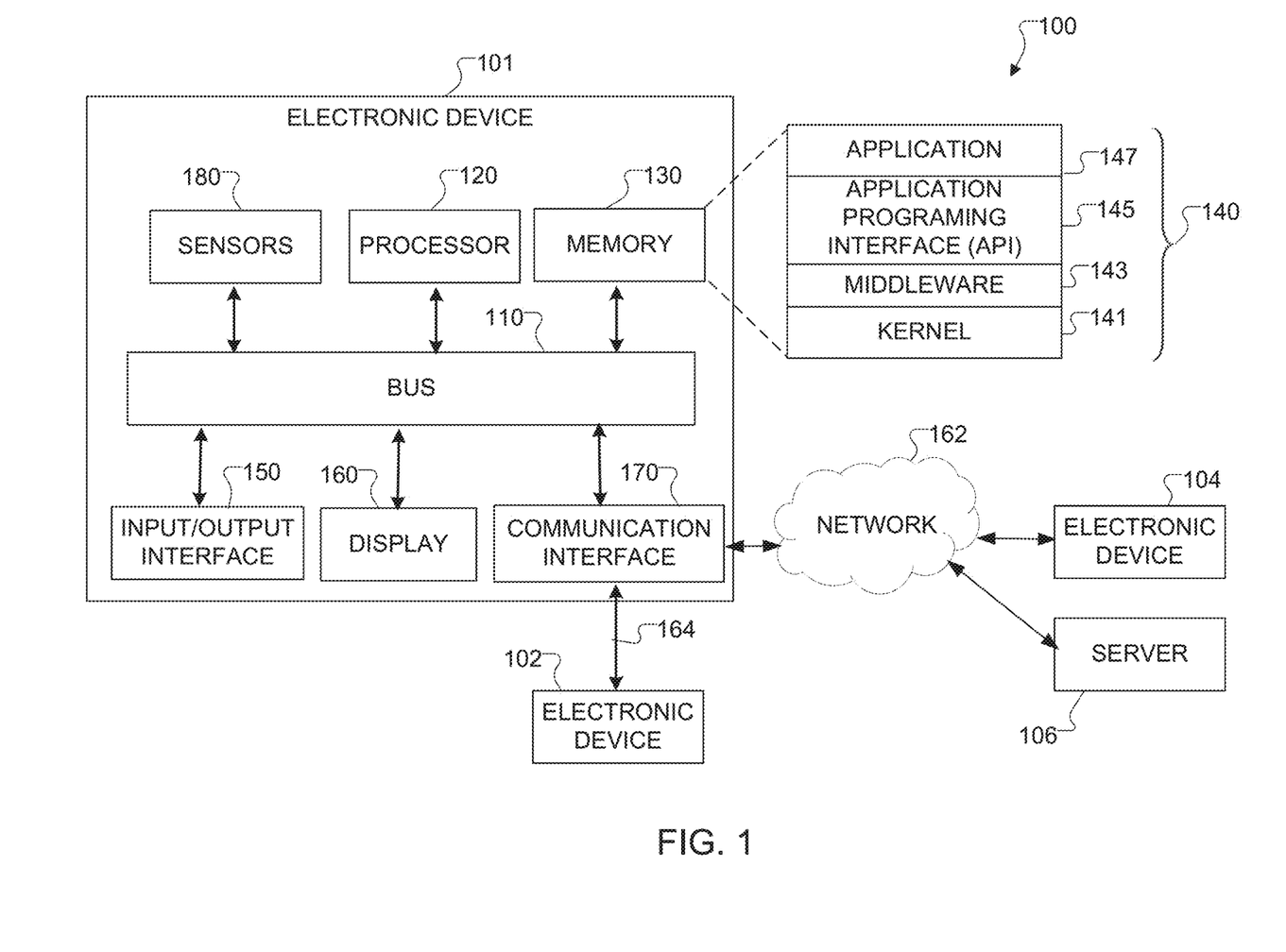
FIG. 1 illustrates an example network configuration in accordance with this disclosure.

FIG. 1 illustrates an example network configuration 100 in accordance with this disclosure. As shown in FIG. 1, according to embodiments of this disclosure, an electronic device 101 is included in the network configuration 100. The electronic device 101 may include at least one of a bus 110, a processor 120, a memory 130, an input/output (I/O) interface 150, a display 160, a communication interface 170, or a sensor 180. In some embodiments, the electronic device 101 may exclude at least one of the components or may add another component.

The bus 110 may include a circuit for connecting the components 120-180 with one another and transferring communications (such as control messages and/or data) between the components. The processor 120 may include one or more of a central processing unit (CPU), an application processor (AP), or a communication processor (CP). The processor 120 may perform control on at least one of the other components of the electronic device 101 and/or perform an operation or data processing relating to communication.

The memory 130 may include a volatile and/or non-volatile memory. For example, the memory 130 may store commands or data related to at least one other component of the electronic device 101. According to embodiments of this disclosure, the memory 130 may store software and/or a program 140. The program 140 may include, for example, a kernel 141, middleware 143, an application programming interface (API) 145, and/or an application program (or "application") 147. At least a portion of the kernel 141, middleware 143, or API 145 may be denoted an operating system (OS).

The kernel 141 may control or manage system resources (such as the bus 110, processor 120, or memory 130) used to perform operations or functions implemented in other programs (such as the middleware 143, API 145, or application program 147). The kernel 141 may provide an interface that allows the middleware 143, API 145, or application 147 to access the individual components of the electronic device 101 to control or manage the system resources. The middleware 143 may function as a relay to allow the API 145 or the application 147 to communicate data with the kernel 141, for example. A plurality of applications 147 may be provided. The middleware 143 may control work requests received from the applications 147, such as by allocating the priority of using the system resources of the electronic device 101 (such as the bus 110, processor 120, or memory 130) to at least one of the plurality of applications 147. The API 145 is an interface allowing the application 147 to control functions provided from the kernel 141 or the middleware 143. For example, the API 133 may include at least one interface or function (such as a command) for file control, window control, image processing, or text control.

The input/output interface 150 may serve as an interface that may, for example, transfer commands or data input from a user or other external devices to other component(s) of the electronic device 101. Further, the input/output interface 150 may output commands or data received from other component(s) of the electronic device 101 to the user or the other external devices.

The display 160 may include, for example, a liquid crystal display (LCD), a light emitting diode (LED) display, an organic light emitting diode (OLED) display, an active matrix OLED (AMOLED), a microelectromechanical systems (MEMS) display, or an electronic paper display. The display 160 can also be a depth-aware display, such as a multi-focal display. The display 160 may display various contents (such as text, images, videos, icons, or symbols) to the user. The display 160 may include a touchscreen and may receive, for example, a touch, gesture, proximity, or hovering input using an electronic pen or a body portion of the user.

The communication interface 170 may set up communication between the electronic device 101 and an external electronic device (such as a first electronic device 102, a second electronic device 104, or a server 106). For example, the communication interface 170 may be connected with a network 162 or 164 through wireless or wired communication to communicate with the external electronic device.

The electronic device 101 further includes one or more sensors 180 that can meter a physical quantity or detect an activation state of the electronic device 101 and convert metered or detected information into an electrical signal. For example, one or more sensors 180 can include one or more buttons for touch input, one or more cameras, a gesture sensor, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a biophysical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (R) sensor, an ultrasound sensor, an iris sensor, or a fingerprint sensor. The sensor(s) 180 can also include an inertial measurement unit, which can include one or more accelerometers, gyroscopes, and other components. The sensor(s) 180 can further include a control circuit for controlling at least one of the sensors included here. Any of these sensor(s) 180 can be located within the electronic device 101.

The first external electronic device 102 or the second external electronic device 104 may be a wearable device or an electronic device 101-mountable wearable device (such as a head mounted display (HMD)). When the electronic device 101 is mounted in an HMD (such as the electronic device 102), the electronic device 101 may detect the mounting in the H/D and operate in a virtual reality mode. When the electronic device 101 is mounted in the electronic device 102 (such as the H/ID), the electronic device 101 may communicate with the electronic device 102 through the communication interface 170. The electronic device 101 may be directly connected with the electronic device 102 to communicate with the electronic device 102 without involving with a separate network.

The wireless communication may use at least one of, for example, long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection may include at least one of, for example, universal serial bus (USB), high definition multimedia interface (HDMI), recommended standard 232 (RS-232), or plain old telephone service (POTS). The network 162 may include at least one communication network, such as a computer network (like a local area network (LAN) or wide area network (WAN)), the Internet, or a telephone network.

The first and second external electronic devices 102 and 104 each may be a device of the same type or a different type from the electronic device 101. According to embodiments of this disclosure, the server 106 may include a group of one or more servers. Also, according to embodiments of this disclosure, all or some of the operations executed on the electronic device 101 may be executed on another or multiple other electronic devices (such as the electronic devices 102 and 104 or server 106). Further, according to embodiments of this disclosure, when the electronic device 101 should perform some function or service automatically or at a request, the electronic device 101, instead of executing the function or service on its own or additionally, may request another device (such as electronic devices 102 and 104 or server 106) to perform at least some functions associated therewith. The other electronic device (such as electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

While FIG. 1 shows that the electronic device 101 includes the communication interface 170 to communicate with the external electronic device 102 or 104 or server 106 via the network(s) 162 and 164, the electronic device 101 may be independently operated without a separate communication function, according to embodiments of this disclosure. Also, note that the electronic device 102 or 104 or the server 106 could be implemented using a bus, a processor, a memory, an I/O interface, a display, a communication interface, and an event processing module (or any suitable subset thereof) in the same or similar manner as shown for the electronic device 101.

Although FIG. 1 illustrates one example of a network configuration 100, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
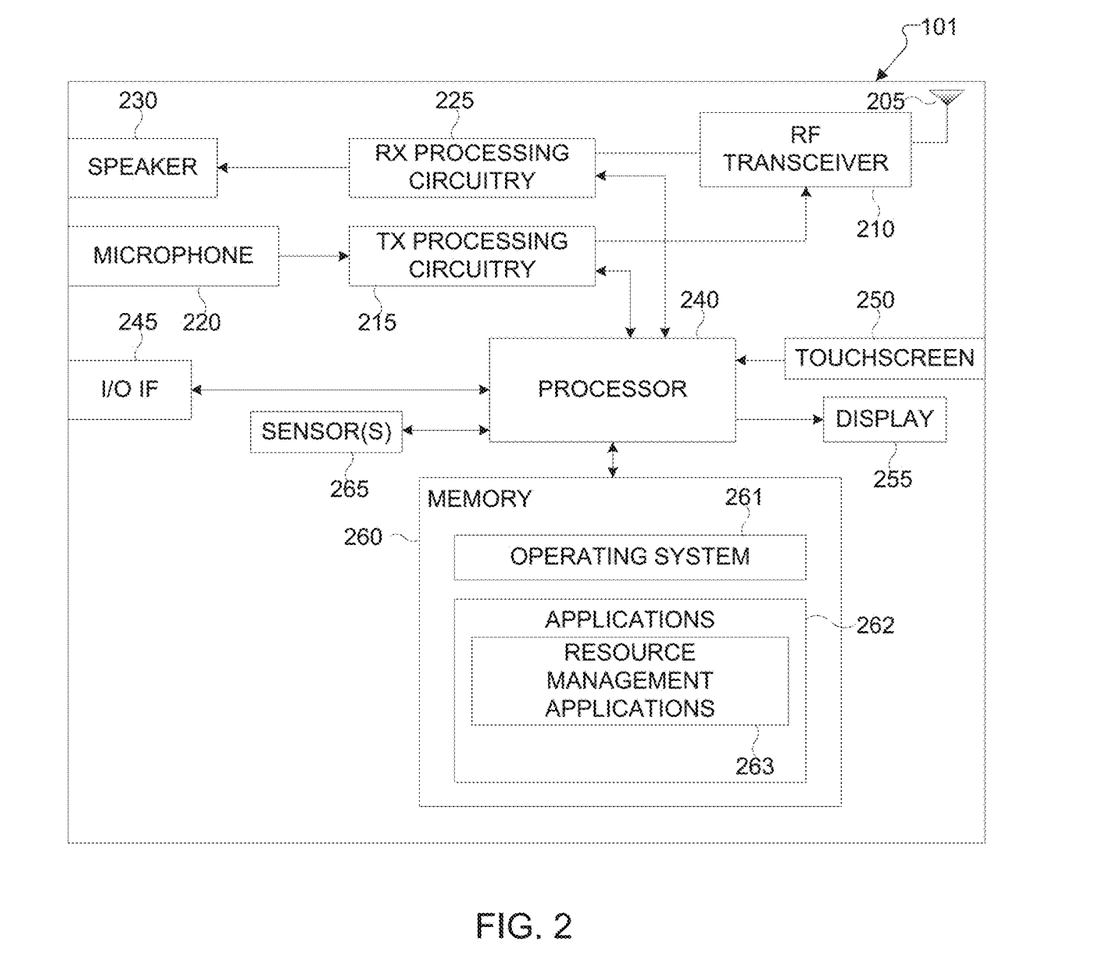
FIG. 2 illustrates an example electronic device in accordance with this disclosure.

FIG. 2 illustrates an example electronic device 101 in accordance with this disclosure. The electronic device 101 could represent one or more of the electronic devices 101, 102, or 104 in FIG. 1. As shown in FIG. 2, the electronic device 101 includes an antenna 205, a radio frequency (RF) transceiver 210, transmit (TX) processing circuitry 215, a microphone 220, and receive (RX) processing circuitry 225. The electronic device 101 also includes a speaker 230, a processor 240, an input/output (I/O) interface (IF) 245, an input 250, a display 255, and a memory 260. The memory 260 includes an operating system (OS) program 261 and one or more applications 262.

The RF transceiver 210 receives, from the antenna 205, an incoming RF signal transmitted by another component in a system. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the processor 240 for further processing (such as for web browsing data).

The TX processing circuitry 215 receives analog or digital voice data from the microphone 220 or other outgoing baseband data (such as web data, e-mail, or interactive video game data) from the processor 240. The TX processing circuitry 215 encodes, multiplexes, and/or digitizes the outgoing baseband data to generate a processed baseband or IF signal. The RF transceiver 210 receives the outgoing processed baseband or IF signal from the TX processing circuitry 215 and up-converts the baseband or IF signal to an RF signal that is transmitted via the antenna 205.

The processor 240 can include one or more processors or other processors and execute the OS program 261 stored in the memory 260 in order to control the overall operation of the electronic device 101. For example, the processor 240 could control the reception of forward channel signals and the transmission of reverse channel signals by the RF transceiver 210, the RX processing circuitry 225, and the TX processing circuitry 215 in accordance with well-known principles. In some embodiments, the processor 240 includes at least one microprocessor or microcontroller.

The processor 240 is also capable of executing other processes and programs resident in the memory 260. The processor 240 can move data into or out of the memory 260 as required by an executing process. In some embodiments, the processor 240 is configured to execute the applications 262 based on the OS program 261 or in response to signals received from external devices or an operator. The processor can execute a resource management application 263 for monitoring system resources. The processor 240 is also coupled to the I/O interface 245, which provides the electronic device 101 with the ability to connect to other devices such as laptop computers, handheld computers and other accessories, for example, a virtual reality (VR) headset. The I/O interface 245 is the communication path between these accessories and the processor 240. The processor 240 can recognize accessories that are attached through the I/O interface 245, such as a VR headset connected to a USB port.

The processor 240 is also coupled to the input 250 and the display 255. The operator of the electronic device 101 can use the input 250 (e.g., keypad, touchscreen, button etc.) to enter data into the electronic device 101. The display 255 may be an LCD, LED, OLED, AMOLED, MEMS, electronic paper, or other display capable of rendering text and/or at least limited graphics, such as from web sites.

The memory 260 is coupled to the processor 240. Part of the memory 260 could include a random access memory (RAM), and another part of the memory 260 could include a Flash memory or other read-only memory (ROM).

The electronic device 101 further includes one or more sensors 265 that can meter a physical quantity or detect an activation state of the electronic device 101 and convert metered or detected information into an electrical signal. For example, the sensor 265 may include any of the various sensors 180 discussed above.

Although FIG. 2 illustrates one example of an electronic device 101, various changes may be made to FIG. 2. For example, various components in FIG. 2 could be combined, further subdivided, or omitted and additional components could be added according to particular needs. As a particular example, the processor 240 could be divided into multiple processors, such as one or more central processing units (CPUs) and one or more graphics processing units (GPUs). Also, while FIG. 2 illustrates the electronic device 101 configured as a mobile telephone or smart phone, electronic devices could be configured to operate as other types of mobile or stationary devices. In addition, as with computing and communication networks, electronic devices can come in a wide variety of configurations and FIG. 2 does not limit this disclosure to any particular electronic device.

Figure 3:
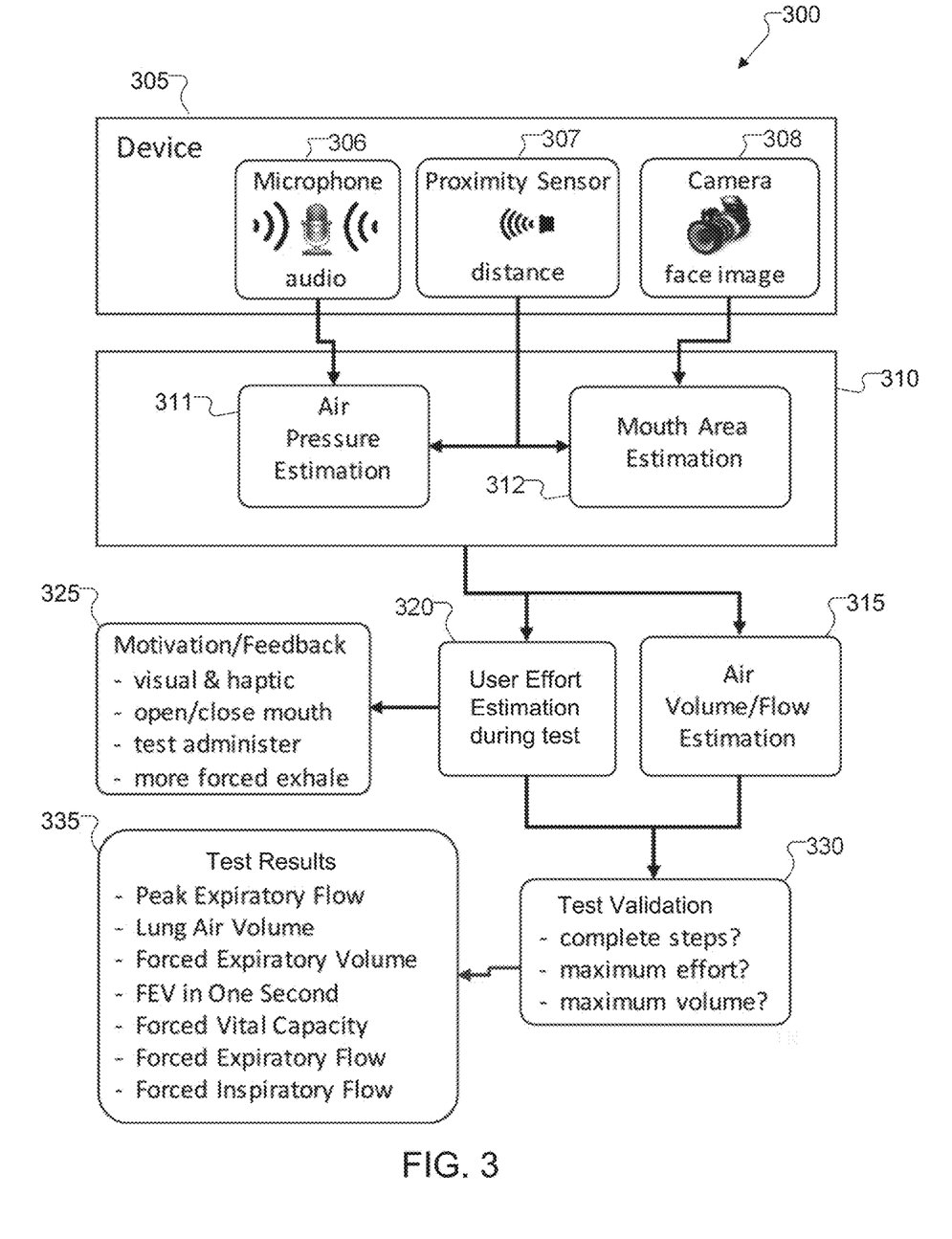
FIG. 3 illustrates an example system for performing an on-device spirometry test in accordance with this disclosure.

FIG. 3 illustrates an example system 300 for performing an on-device spirometry test in accordance with this disclosure. For ease of explanation, the system 300 is described as involving at least one electronic device (such as the electronic device 101 of FIG. 1). However, the system 300 could involve any other suitable device(s) or system(s) without departing from the scope of this disclosure.

As shown in FIG. 3, the system 300 includes a mobile device 305. The mobile device 305 is a mobile electronic device that is associated with (or used by) a user who may have a respiratory condition that can be monitored by a spirometry test. The mobile device 305 may represent one of the electronic devices 101, 102, 104 of FIG. 1. For example, the mobile device 305 may be the user's smart phone, smart watch, or tablet.

The mobile device 305 includes an audio sensor 306 that is capable of detecting and recording audio in the vicinity of the mobile device 305, such as the microphone 220 of FIG. 2. During the spirometry test, the audio sensor 306 can detect and record audio associated with the user breathing, including inhalation and exhalation. The mobile device 305 also includes a proximity sensor 307 that is capable of detecting and recording position and distance relative to another object. The proximity sensor 307 can represent, or be represented by, one or more of the sensors 180 of FIG. 1. During the spirometry test, the proximity sensor 307 can detect and measure a distance from the user's face or mouth to the mobile device 305. The mobile device 305 also includes an image sensor 308 that is capable of detecting and recording images and video, such as a front facing camera. During the spirometry test, the image sensor 308 can detect and record still or video images of the user's face or mouth. Although FIG. 3 illustrates only one of each of the sensors 306-308, other embodiments could include more than one of any or all of the sensors 306-308.

During the spirometry test, the mobile device 305 instructs the user to hold the mobile device in front of the user's face such that the image sensor 308 can detect the user's face. In some embodiments, a preferred distance between the user's face and the mobile device 305 is approximately fifteen centimeters, although the distance may vary during the test and shorter and longer distances are within the scope of this disclosure. The mobile device 305 instructs the user to inhale and exhale near the audio sensor 306. As with most spirometry tests, the test is most accurate when the user inhales deeply and then exhales quickly and completely. A typical spirometry test lasts approximately six seconds, although the time could be shorter or longer, depending on the user. As the user inhales and exhales, the audio sensor 306 captures the sound created by the air flow and pressure and converts the sound into sound data. Likewise, the proximity sensor 307 detects and determines the distance from the mobile device 305 to the user's face, and the image sensor 308 records still or video images of the user's face or mouth. Using the sound data, distance data, and image data obtained during the spirometry test, the mobile device performs multiple estimation functions 310, including an air pressure estimation function 311 and a mouth area estimation function 312.

Figure 4:
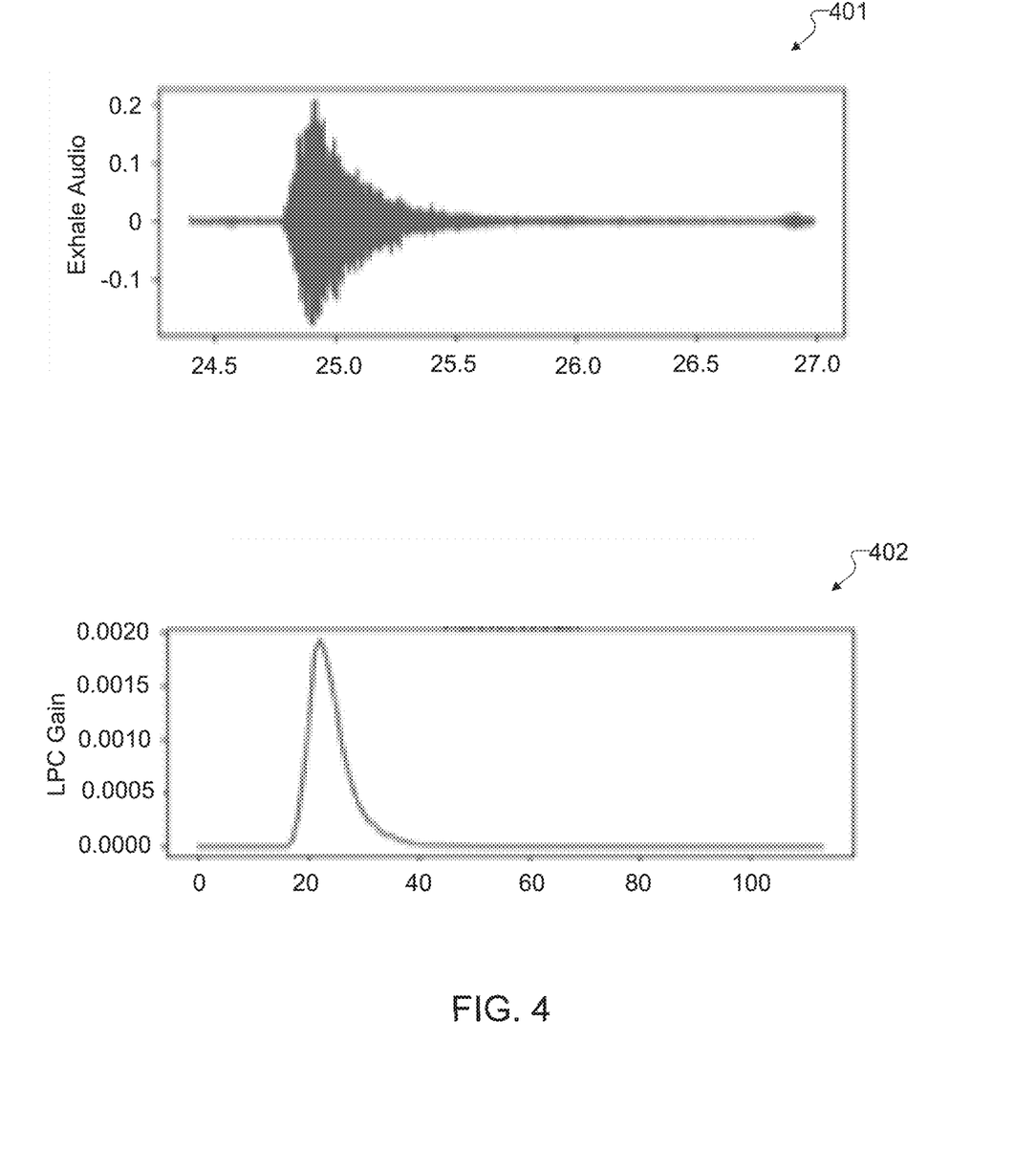
FIG. 4 illustrates an example plot of an air pressure curve and an example plot of Linear Predictive Coding (LPC) gain of audio obtained during the spirometry test in accordance with this disclosure.

In the air pressure estimation function 311, the mobile device 305 uses audio signal processing to detect and extract the inhalation and exhalation sections of the sound data and estimate the air pressure created during each section by analyzing the energy level and frequency features of the audio. In some embodiments, the mobile device 305 extracts information regarding air flow and air pressure by analyzing the Linear Predictive Coding (LPC) features of the audio during the inhalation and exhalation process. For example, FIG. 4 illustrates an example plot 401 of an air pressure curve and an example plot 402 of LPC gain of the audio obtained during a spirometry test in accordance with this disclosure. Since the LPC features extracted from the audio lie in the low-mid range of frequency spectrum, the LPC are quite reliable even when audio is captured behind the screen of the device. In some embodiments, estimation models can be pre-trained using recorded audio from different microphones located in various locations to improve the robustness of the estimation.

In some embodiments, the mobile device 305 can remove background noise by capturing and subtracting the sound profile of the environment. Moreover, the mobile device 305 can ignore noisy sound events (short term or long term) by considering a higher threshold in segmenting out the breathing events of inhalation and exhalation. It is expected that there may be variations in the audio data during different spirometry tests, considering different ways of blowing near the device. In certain embodiments, the mobile device 305 accounts for these variations and avoids the steps of distance/volume calibration by using other context data such as captured images of subject mouth/face and distance between face and device, as explained in greater detail below.

In the mouth area estimation function 312, the mobile device 305 uses the image data from the image sensor 308, the distance data from the proximity sensor 307, and one or more image processing techniques to estimate the area of the opening of the mouth while the user inhales and exhales during the spirometry test. The mobile device 305 uses the estimated area of the mouth in measuring the amount of air volume exchange. This is due to the fact that the area of the mouth while inhaling and exhaling influences the air pressure and thereby the amount of air volume exchange. Furthermore, mouth area data constitutes personalized data of each user while conducting the test. This feature enables the mobile device 305 to account for subject-to-subject variations. Therefore, mouth shape calibration or subject training before the spirometry test can be avoided while improving the accuracy of the results. This is important for an accurate measurement since there may be no medical supervision of the user while the user conducts the test.

Estimation of a shape in an image and estimation of the area of that shape has intrinsic error due to the challenges of image processing. For instance, the area of the mouth could be calculated differently depending on the distance of the face from the front camera. Therefore, the mobile device 305 considers the estimated distance between the user's face and the device 305 in the mouth area estimation function 312 to compensate for this possibility.

The mobile device 305 can use any of several possible techniques for distance estimation. For example, as discussed above, the mobile device 305 can use distance data from the proximity sensor 307. In some embodiments, the mobile device 305 could additionally or alternatively use data from a personal image profile. In such a profile, a pre-obtained baseline image of the user's face at a fixed distance would be established as the reference point for estimating the mouth area and distance from the device. In some embodiments, the mobile device 305 could use data from one or more internal motion sensors to measure the geometric distance between the mobile device 305 and the user's mouth by identifying the upper-arm length, position and orientation of the mobile device 305 with respect to a body coordinate system centered at the shoulder of the user. The distance can be estimated while moving the mobile device 305 from face or pocket to the requested location facing the user's face. As another example, depth-field cameras may provide the distance information of the user's face in the camera image. As yet another example, a mechanical aid, such as a string or band, between the user and the mobile device 305 can be used to maintain a constant distance between the user's face and the mobile device 305

It is noted that, in some embodiments of the spirometry test, the user may place the user's mouth around a mouth piece during inhalation and exhalation. In such an embodiment, the cross-sectional area of the mouth piece may be known by the mobile device 305, in which case, estimation of the mouth area would not be needed.

After the mobile device 305 has estimated the air pressure and mouth area during the spirometry test, the mobile device 305 performs an air volume/flow estimation function 315 to measure the amount of air volume exchange during exhalation and inhalation. The air volume exchange is measured by estimating the air flow in and out of the mouth. That is, the mobile device 305 uses one or more of the recorded audio, the mouth/face image data, and the distance from the user's face to the mobile device 305 to estimate the amount of air volume exchange during the spirometry test. In some embodiments, the air volume exchange can be empirically inferred from features of the captured audio and image data or by training a regression or machine learning model that captures the relationship. The mobile device 305 tracks the amount of air volume exchange for the whole duration of the spirometry test. The mobile device 305 can accurately estimate the amount of air volume exchange without the need for complicated device calibration by the user.

The mobile device 305 estimates the amount of air volume exchange, which is directly correlated with the air flow and pressure and the mouth opening area, as shown in the following, given the assumption that the user's effort is at its maximum (i.e., the user's air flow during the spirometry test is at or close to the maximum amount possible by the user):

$$Q[\text{air volume exchange}] = v[\text{air flow}] \times A[\text{mouth area}] \quad (1)$$

where, e.g., Q can have units of liters/second, v can have units of meters/second, and A can have units of $cm^2$.

After estimating the amount of air volume exchange during the test, the mobile device 305 also determines one or more pulmonary function parameters, such as Peak Expiratory Flow (PEF), Maximal Expiratory Flow (MEF), Forced Expiratory Volume (FEV), FEV in One Second (FEV1), Forced Vital Capacity (FVC), Forced Expiratory Flow (FEF), and Forced Inspiratory Flow (FIF). These parameters represent the lung health of the user and should be in a certain range considering the user's lung condition.

Figure 5:
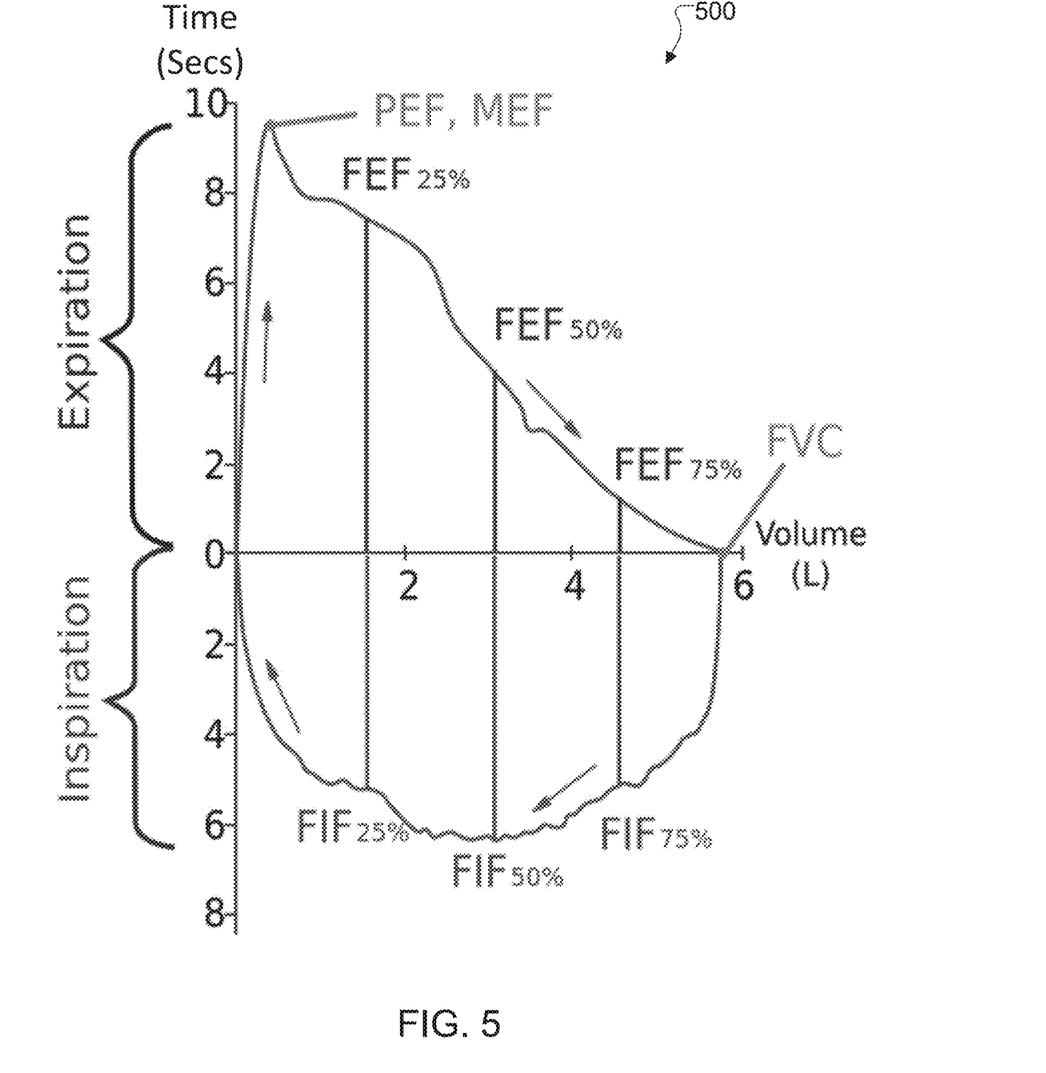
FIG. 5 illustrates an example air flow/volume curve with multiple pulmonary function parameters evaluated after a complete spirometry test in accordance with this disclosure.

FIG. 5 illustrates an example air flow/volume curve 500 with multiple pulmonary function parameters indicated after a complete spirometry test in accordance with this disclosure. The mobile device 305 processes the curve 500 and the temporal data to extract the pulmonary function parameters, which indicate the user's pulmonary health condition. The mobile device 305 can use any suitable techniques or algorithms to determine each of the pulmonary function parameters. The values for the pulmonary function parameters can be compared with statistics and normal values in order to provide a higher-level summary to the user in terms of the user's overall lung health. For instance, the value of the FEV1/FVC ratio can be used to classify the user's lung health into different severity levels (e.g., mild, moderate, and severe).

After the mobile device 305 has estimated the air pressure and mouth area during the spirometry test, the mobile device 305 also performs a user effort estimation function 320 to determine the amount of effort by the user during the spirometry test. In particular, the mobile device 305 uses the air pressure and face features estimated during the inhalation and exhalation process to determine the amount of effort that the user put into the test, map to the user's stress level, and compare to the user's maximum baseline. The mobile device 305 uses the amount of the user's effort estimated over time to provide feedback and, e.g., guide the user to adjust the way the user conducts the test or motivate the user to accomplish a correct test.

A common challenge of conventional spirometry solutions is the difficulty of having the subject perform the spirometry test correctly. For maximum success, the subject is required to fully inhale, and then forcefully exhale into the device with their highest effort. Failure to do these steps correctly can result in decreased accuracy. In a medical setting, a trained clinician or pulmonologist may be available to guide the subject through the test. The clinician or pulmonologist may ask the subject to retry the test multiple times in order to get their best effort. In in-home or other portable spirometry tests, medical personnel may not be available and the effort of the subject is not evaluated. Thus, the subject is not properly notified of the subject's lack of effort during the test. Moreover, current solutions for in-home spirometry consider rule-based techniques which do not properly represent the effort of subjects and they may fail to provide accurate test results.

In contrast, in the system 300, the mobile device 305 uses the recorded audio, the mouth/face image of the user, the distance from the user's face to the mobile device 305, or a combination of these, in order to quantify the effort put into inhalation and exhalation by the user. The mobile device 305 continuously measures the effort by the user during the spirometry test to ensure maximum effort throughout the test. In some embodiments, the mobile device 305 estimates the probability that the user is completely filling up his or her lung capacity when inhaling and emptying it out when exhaling, thus resulting in maximum air volume exchange. In addition, the mobile device 305 estimates the probability that the user is using maximum force while exhaling, resulting in the maximum air flow and pressure. The mobile device 305 then uses these metrics to quantize the user effort, and guide or motivate the user to increase the user's effort or adjust the user's technique in performing the test. In general, user effort can be demonstrated in the following factors:

Facial Features: The location, shape, or color of the subject's mouth, jaw, or eyes may change depending on the amount of effort put into inhalation and exhalation. It has been shown that blowing effort and the stress of the test can influence the blood perfusion and face skin color depending on the pressure put on the subject.

Recorded Audio: The energy, duration, or frequency features of the recorded audio would be affected depending on the effort put into exhalation and inhalation. This is due to the fact that the forced muscle activation would change the size of the vocal cords and tubes resulting in different resonances, which can be demonstrated in change of audio frequency features.

Stress Level: It has been shown that the stress level can be passively measured by a photoplethysmogram (PPG) sensor, which is an included component of some mobile devices. Therefore, the self-reported effort values and stress level activity can be used as potential ground truths and target values in training the user effort estimation models.

Based on some or all of these factors, the mobile device 305 can perform the user effort estimation function 320 to determine a level of user effort while the user performs the spirometry test. For example, using machine learning techniques, the mobile device 305 maps the facial features and audio features and their changes during the test to one or more quantity metrics indicating the user's effort. This effort can be compared to the user's baseline, and the comparison can be used to ensure that the user maintains maximum effort throughout the test. The quantity metrics represent the percentage and probability of maximum possible air volume exchange and maximum possible air flow. These mappings can be captured empirically or by training a regression or machine learning model, as indicated by the formulas below.

$$f_{train}(\text{stress level, effort}) \to P[\text{max air vol exchange}] \sim f(x_{face\ shape}, x_{recorded\ audio}) \quad (2)$$

$$f_{train}(\text{stress level, effort}) \to P[\text{max air flow}] \sim f(x_{face\ shape}, x_{recorded\ audio}) \quad (3)$$

Based on the amount of user effort estimated in the user effort estimation function 320, the mobile device 305 may provide real-time feedback 325 to the user during or after the spirometry test. Typically, in medical settings, subjects are trained before a spirometry test or they are motivated by clinicians during the test to ensure their maximum effort is put into the test. However, medical supervision is usually not possible for portable spirometry. To address this, the mobile device 305 provides the real-time feedback 325 to guide the user to adjust a behavior to maximize or improve the user's effort and possibly prevent multiple attempts of the spirometry test. The approaches used to provide the feedback 325 to the user can vary depending on the scenario, user, and motivation of the feedback. For example, the feedback 325 provided by the mobile device 305 can include one or more of the following:

Visual Feedback: The mobile device 305 can show messages or instructions, such as "Exhale!", on the display of the mobile device 305 to instruct or guide the user while performing the test. In some embodiments, the mobile device 305 can provide augmented reality (AR) visual feedback on the front camera image that guides the user to: 1) open/close their mouth further, or 2) get closer to or farther from the device. This can include graphical indicators, such as arrows, superimposed on the camera image of the user's mouth. Other visual feedback can include interactive motion graphics that motivate the user to increase and continue their effort during the test, if low effort has been detected. For instance, the user can be encouraged to increase the user's air flow force.

Haptic Feedback: The mobile device 305 can use haptic feedback (e.g., use of vibrations) to notify and guide the user to continue his or her effort during the test and to stop the test. In some embodiments, the intensity or duty cycle of the vibration can indicate the user's effort and support the user during the test as a motivating component.

Audio Feedback: The mobile device 305 can generate one or more sounds (e.g., beeps, buzzes, rings, spoken language sounds, and the like) to notify the user of any error or to encourage the user during the spirometry test. For example, a pulsing sound can be used to give feedback on the intensity of the effort made by the user.

After the mobile device 305 has estimated the air volume exchange and the amount of user effort, the mobile device 305 performs a test validation function 330 to determine if the spirometry test was completed correctly. In general, spirometry tests are typically accurate, unless the subject did not properly conduct the test. In medical settings, any mistakes are typically noticed by a clinician. However, for in-home spirometry, the challenge would be to identify the mistakes by looking at only the measurements. Conventional in-home spirometry solutions consider rule-based techniques that monitor the curve of the air flow during the test. However, they may fail in validation of the test and identifying any mistakes, as the air flow curve does not fully represent the way the subject performed the test; instead, the air flow curve is an output of the test, which may be affected by personal health condition or test imperfection.

To address this, the mobile device 305 performs the test validation function 330 to determine if the spirometry test was completed correctly or if any mistakes were made by the user during the test. In particular, the test validation function 330 utilizes one or more of recorded audio, mouth/face images, or distance from face to device during the test to validate the test and identify any mistakes made by the user during exhalation or inhalation. In the test validation function 330, the mobile device 305 compares the quantified user effort curve over the time of the test to the air flow volume curve. These features should correlate and match each other, and at the same time should validate the following criteria in order to ensure a complete and correct spirometry test:

Acceptable position of device against face/mouth during the test.

Acceptable pattern of inhalation and forced exhalation.

Maximum effort by the user throughout the test.

Sensible air volume exchange during the test (intake volume>=exhale volume).

If any of the above criteria are not correct, this can be indicative of a mistake performed by the user during the test. The mobile device 305 performs the test validation function 330 to identify the type and time of any mistakes made by the user. Mistakes can include, e.g., early termination of the test, lack of effort by the user at any time during the test, inconsistent air flow, air volume mismatch (i.e., the amount of air exhaled by the user is not the same as the amount of air inhaled), and the like.

In some embodiments, the test validation function 330 includes an anomaly detection algorithm for each of the above criteria to identify the mistakes and amount of misalignment. In some embodiments, the test validation function 330 generates an overall score to represent the amount of correctness and completeness of the test. This score is estimated using the above-mentioned features and criteria extracted from the recorded data. The mobile device 305 can map the score from these features to a scalar value by training a regression or machine learning model. In some embodiments, the criteria and variables that had a significant influence on the value drop of the score are identified as the mistakes during the test. The mobile device 305 can provide the results of the test validation function 330 to the user as feedback, including any identified mistakes, so that the user can adapt their way of conducting the test.

In addition to reporting the results of the test validation function 330, the mobile device 305 also reports test results 335 to the user. The test results 335 can include the user effort curve over the time of the test, the air flow volume curve, the amount of air volume exchange, one or more of the pulmonary function parameters (PEF, MEF, FEV, FEV1, FVC, FEF, FIF), or any combination of these. In some embodiments, the values of the pulmonary function parameters can be compared with statistics and normal values in order to provide a higher-level summary to the user as an indicator of the user's overall lung health. For instance, the value of the FEV1/FVC ratio can be used to classify the user's lung health into different severity levels (e.g., mild, moderate, and severe).

The mobile device 305 can show the test results 335 on the display of the mobile device 305, or the mobile device 305 can send the test results 335 to another device (e.g., a medical clinic server) for evaluation by a medical professional. The test results 335 can be used by the user or the medical professional for diagnostic or treatment purposes. In some embodiments, the test results 335 can improve treatment or make treatment more efficient by providing more frequent, more accurate spirometry information. For example, the test results 335 could reveal a breathing condition that, if observed early, would result in less significant medical treatment (e.g., less medication), but if not diagnosed until later, might result in asthma attack or exacerbation that would require more significant treatment (e.g., more medication or even surgery), admission to an emergency room, or hospitalization.

Although FIG. 3 illustrates one example of a system 300 for performing an on-device spirometry test, various changes may be made to FIG. 3. For example, the system 300 could be implemented in any suitable manner, such as entirely within the mobile device 305 or using a combination of devices. As a particular example, at least some of the functions and operations can be implemented or supported using one or more software applications or other software instructions that are executed by one or more processor(s) 120, 240 of the mobile device 305. In other embodiments, at least some of the functions and operations can be implemented or supported using dedicated hardware components. In general, the functions and operations can be performed using any suitable hardware or any suitable combination of hardware and software/firmware instructions. In some embodiments, the mobile device 305 could collect the audio, image, and proximity data and provide the data to a server 106, which could then perform some of the operations of FIG. 3. Results of the processing could then be made available to the mobile device 305 and/or one or more other devices (such as the electronic device 102 or 104). In general, computing and communication systems come in a wide variety of configurations, and FIG. 3 does not limit the scope of this disclosure to any particular configuration.

Other possible changes to FIG. 3 include one or more of the following, which are within the scope of this disclosure.

In a case where one or more wearable devices include the sensors 306-308, the spirometry test can be conducted exclusively on the wearable devices by holding the wearable devices facing the user and blowing into them. The various data collection and processing functions of the system 300 would be the same or similar on the wearable devices as on the mobile device 305. In some embodiments, the mobile device 305 and a wearable device could complement each other in the spirometry test. For example, sensor data from both the mobile device 305 and the wearable device can be collected together and time synchronized, such that the fused sensor data is used for evaluating the results. As a particular example, a smart phone can be held with the hand that is wearing a smart watch when the spirometry test is conducted. The audio, image, or sensory data (for distance) collected from both devices would complement each other, and may improve the accuracy of the results.

In some embodiments, the amount of air volume exchange can be estimated in various ways using alternative methods. For example, one or more motion sensors of the mobile device 305 or a wearable device can be used to measure the user's chest movements when conducting the spirometry test. The chest movements can be used to estimate air volume exchange and later mapped to the pulmonary function parameters and air volume. As another example, one or more contactless sensors (e.g., infrared sensor, thermal imaging sensor, etc.) or other cameras can estimate lung parameters when the user is performing the spirometry test in front of the sensors. A heatmap or images generated by these sensors can be used to measure the chest movements when conducting the test. The chest movements can be used to estimate air volume exchange and later mapped to the pulmonary function parameters.

In some embodiments, image and audio data can be captured using a device other than the mobile device 305 or a wearable device. For example, an external camera placed in proximity to the user can record audio or image data of the user conducting the test. The external camera can then send the data to the mobile device 305 so that the mobile device 305 can process the data and evaluate the results. As another example, video and audio recorded through other software technologies, such as a video chat tool, can be used for evaluating results.

In some embodiments, when the user performs the spirometry test on a mobile device, it can be important or necessary to identify the forced exhalation in the continuous mobile sensor data before the lung function biomarkers, such as FEV1, FVC, FEV1/FVC, PEF, or the like, are estimated. The presence of the forced exhalation can be estimated in continuous mobile sensor time series data using a template-based algorithm described below or using one or more machine learning algorithms such as Random Forest, Logistic Regression, XGBoost, Support Vector Machine, or the like, by performing left out validation.

In some embodiments, how hard the user forces his or her exhalation can greatly affect the reliability of the lung function biomarker measurement. Therefore, it is advantageous to estimate the quality of the effort captured by mobile sensor data. In some embodiments, the detection and effort quality assessment can be performed together or in succession. In one embodiment, a window of 6-second audio is detected as a forced exhalation segment. The start of the exhalation can be further pinpointed by removing the initial silence based on an empirically learned energy threshold. It is noted that the audio of the forced exhalation is mostly audible in the first 2-3 seconds out of a 6 second effort. Therefore, the Time To Peak Flow (TTPF) is an quality parameter for mobile spirometry. From observing the distribution of the TTPF analysis from a training dataset, it is noted that the high quality efforts' TTPF may go up to 400 milliseconds. If the TTPF is more than 400 milliseconds, it is considered a poor effort and may be discarded from the assessment.

To ensure that high quality efforts are detected and appropriate feedback is provided to the user who is using the smartphone spirometry at home without any clinician supervision, the system 300 can further analyze the shape of the envelope of a forced expiratory effort sound. In some embodiments, a shape based time series data modeling approach is used to detect a template of the forced exhalation sounds from the rigorously annotated sound segments. A percentile based approach to generate an individual envelope performs better than traditional approaches, such as maximum value or root mean square (RMS) based approaches. The system 300 can compute the mean of the individual envelopes from the training data to generate the template envelope for high fidelity forced expiratory effort sounds.

The similarity between the template and the individual envelope can be used as a metric for mobile spirometry. The similarity can be computed as the absolute distance between the template (which is the expected shape) and the envelope from individual forced expiratory sound segments as described in the equations below. First, the construction of the template is described as:

$$T[n] = \frac{1}{K}\sum_{k=1}^{K} Env_k[n], \forall n \in [1, N]$$

where $T[n]$ is the nth sample of the envelope template T, $Env_k[n]$ is the nth sample of the kth envelope $Env_k$ in the training set, K is the total number of envelopes that have an available sample at the nth position, and N is the total number of samples in the longest envelope. The distance metric is then computed as the absolute difference between each of the data points of the current envelope $Env_c$ and the template envelope T as the equation given below:

$$D = \sum_{i=1}^{M} \|Env_c[i] - T[i]\|$$

where M is the total number of samples in the current envelope $Env_c$ and it is assumed that M<=N, where N is the total number of samples in the template T.

Figure 6:
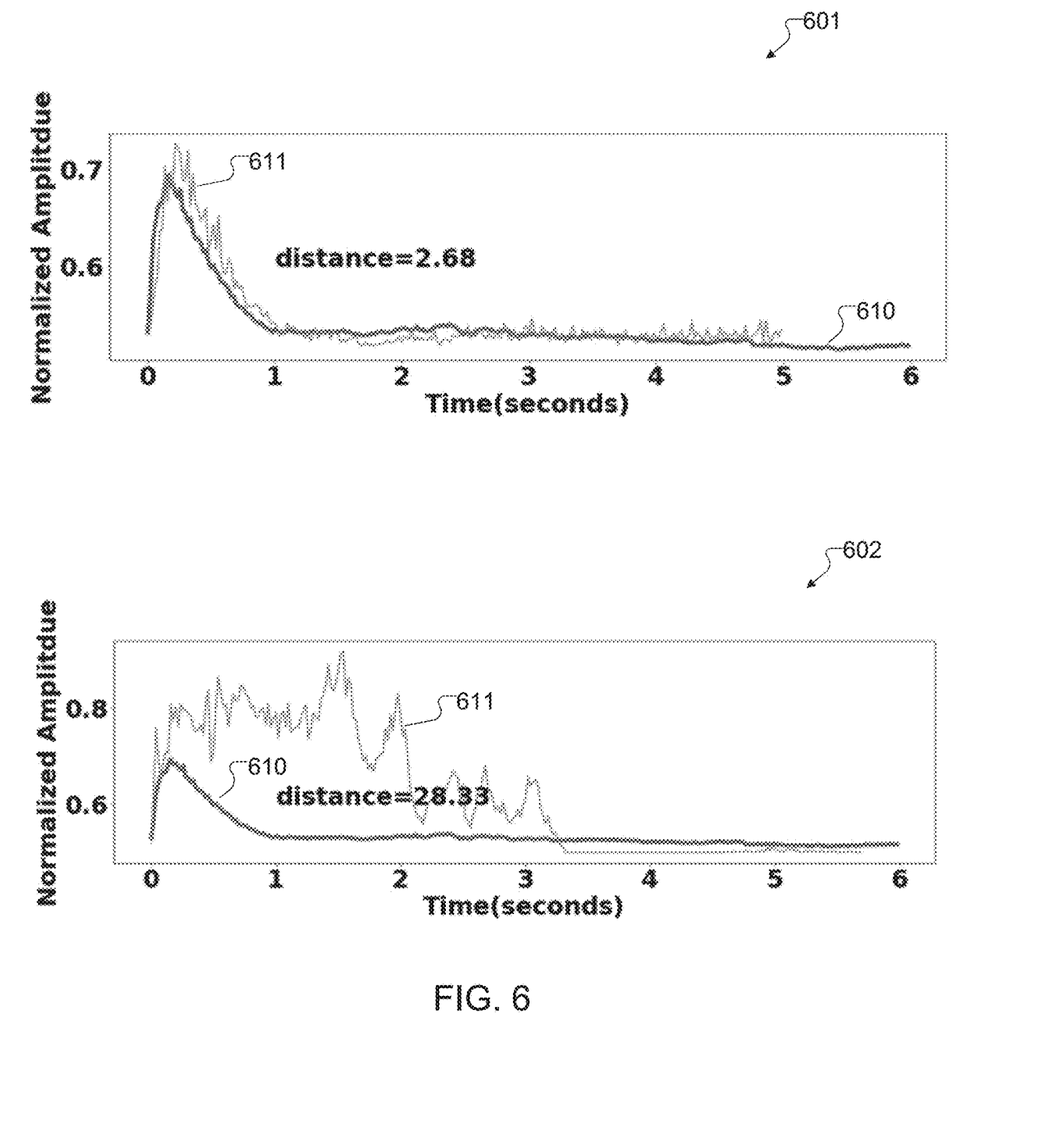
FIG. 6 illustrates two plots showing a similarity between a template and a current forced exhalation from a spirometry test in accordance with this disclosure.

FIG. 6 illustrates two plots 601-602 showing a similarity between the template and the current forced exhalation from a spirometry test in accordance with this disclosure. From the dataset, the similarity metric is computed for all the smartphone spirometry efforts, and the distribution of the distance is plotted.

As shown in FIG. 6, the distance from the template can help identify the expected effort from a poor effort. The plot 601 shows low distance and high similarity, while the plot 602 show high distance and low similarity. In each plot 601-602, the curve 610 represents the template envelope and the curve 611 represent the current effort under investigation. It can be observed that the higher the distance, the lower the quality of the effort. It can also be observed that a similarity distance more than a certain threshold can divide the high quality efforts from the poor efforts. Other embodiments can use other important features such as correlation, variance, mean, with the distance metric to train a machine learning model to identify high quality effort from the poor efforts. The user interface can provide the guidance based on the detected effort quality to the user to try again to produce a reliable lung function measurement.

Figure 7:
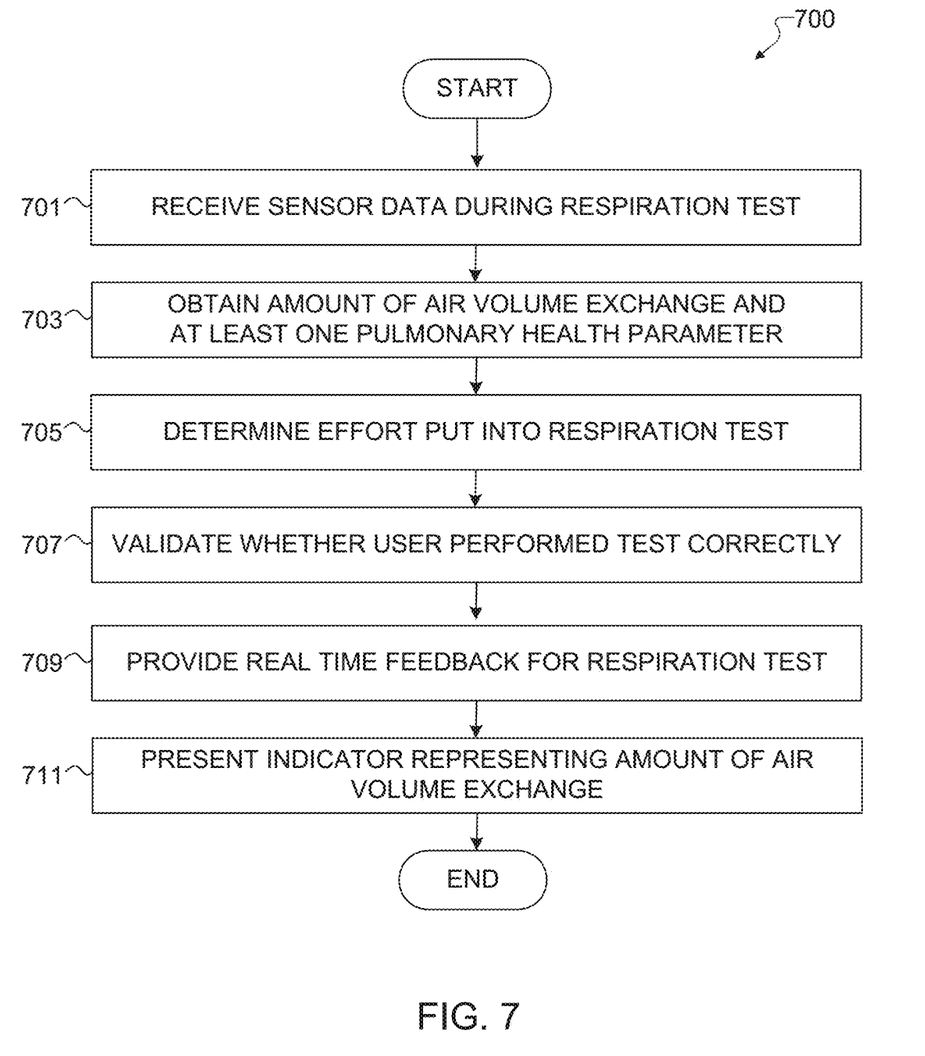
FIG. 7 illustrates an example method for performing an on-device spirometry test in accordance with this disclosure.

FIG. 7 illustrates an example method 700 for performing an on-device spirometry test in accordance with this disclosure. For ease of explanation, the method 700 shown in FIG. 7 is described as involving the use of the mobile device 305 of FIG. 3. However, the method 700 shown in FIG. 7 could be used with any other suitable electronic device and in any suitable system.

At operation 701, the mobile device 305 receives sensor data during a spirometry test of a user. The sensor data includes audio data of the user and distance data of a distance from a face of the user to the mobile device 305. This can include, for example, the mobile device 305 receiving audio data from the audio sensor 306 and receiving distance data from the proximity sensor 307. In some embodiments, the sensor data further includes image data of the face of the user. The image data can be received from the image sensor 308.

At operation 703, the mobile device 305 obtains an amount of air volume exchange and at least one pulmonary health parameter that are determined based on the audio data and the distance data. In some embodiments, the amount of air volume exchange and the at least one pulmonary health parameter are further determined based on the image data. This can include, for example, the mobile device 305 determining the amount of air volume exchange and the at least one pulmonary health parameter by performing the air volume/flow estimation function 315. Alternatively, this can include the mobile device 305 receiving the amount of air volume exchange and/or at least one pulmonary health parameter from another device, such as the server 106, after the other device determines the amount of air volume exchange and the at least one pulmonary health parameter.

At operation 705, the mobile device 305 determines an amount of effort put into the spirometry test by the user based on at least one of the audio data, the image data, and the distance. This can include, for example, the mobile device 305 performing the user effort estimation function 320 to determine the amount of effort put into the spirometry test by the user.

At operation 707, the mobile device 305 validates whether the user performed the spirometry test correctly. This can include, for example, the mobile device 305 performing the test validation function 330 to determine whether the user performed the spirometry test correctly.

At operation 709, the mobile device 305 provides real time feedback after validating that the user did not perform the spirometry test correctly. This can include, for example, the mobile device 305 providing visual feedback, audio feedback, haptic feedback, or any combination of these, to the user. The feedback can identify any mistakes performed by the user during the test and provide corrective actions for the user to take.

At operation 711, the mobile device 305 presents an indicator on a display of the mobile device 305 for use by the user or a medical provider, where the indicator represents the amount of air volume exchange. This can include, for example, the mobile device 305 presenting one or more of the test results 335 on the display of the mobile device 305. The test results 335 can include the user effort curve over the time of the test, the air flow volume curve, the amount of air volume exchange, one or more of the pulmonary function parameters (PEF, MEF, FEV, FEV1, FVC, FEF, FIF), or any combination of these.

Although FIG. 7 illustrates one example of a method 700 for performing an on-device spirometry test, various changes can be made to FIG. 7. For example, various steps in FIG. 7 could overlap, occur in parallel, occur serially, occur in a different order, or occur any number of times. Also, the steps of the method 700 could be implemented in any suitable manner, such as entirely within the mobile device 305 or using a combination of devices. For instance, as indicated above, the mobile device 305 could collect data and provide the data to a server 106, which could then process the data and generate any suitable output.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method, comprising:
receiving, by an electronic device during a spirometry test of a user, (i) audio data of the user from at least one audio sensor of the electronic device, (ii) image data of a mouth of the user from at least one image sensor of the electronic device, and (iii) distance data from at least one proximity sensor of the electronic device, the distance data indicating a distance from the mouth of the user to the electronic device, wherein the audio data, the image data, and the distance data are received concurrently while the user inhales and exhales during the spirometry test;
determining, by the electronic device, an amount of air volume exchange and at least one pulmonary health parameter as a function of the audio data, the image data, and the distance data; and
presenting an indicator on a display of the electronic device, the indicator representing the amount of air volume exchange.

2. The method of claim 1, further comprising:
determining an amount of effort put into the spirometry test by the user based on at least one of the audio data, the image data, and the distance data.

3. The method of claim 1, wherein the at least one pulmonary health parameter comprises at least one of: peak expiratory flow (PEF), forced expiratory volume (FEV), FEV in one second (FEV1), forced vital capacity (FVC), forced expiratory flow (FEF), or forced inspiratory flow (FIF).

4. The method of claim 1, further comprising:
validating, by the electronic device, whether the user performed the spirometry test correctly; and
providing, by the electronic device, real time feedback after validating that the user did not perform the spirometry test correctly.

5. The method of claim 4, wherein the real time feedback indicates at least one mistake performed by the user during the spirometry test, the at least one mistake comprising at least one of: early termination of the spirometry test, an amount of effort by the user during the spirometry test being less than a baseline amount, inconsistent air flow by the user, or an air volume mismatch by the user.

6. The method of claim 4, wherein the real time feedback comprises an instruction to the user to perform the spirometry test again.

7. The method of claim 4, further comprising:
providing, by the electronic device, second real time feedback during the spirometry test, the second real time feedback comprising at least one instruction to the user to adjust a behavior during the spirometry test.

8. An electronic device comprising:
at least one audio sensor;
at least one image sensor;
at least one proximity sensor;
a processor configured to:
receive, during a spirometry test of a user, (i) audio data of the user from the at least one audio sensor, (ii) image data of a mouth of the user from the at least one image sensor, and (iii) distance data from the at least one proximity sensor, the distance data indicating a distance from the mouth of the user to the electronic device, wherein the processor is configured to receive the audio data, the image data, and the distance data concurrently while the user inhales and exhales during the spirometry test; and
determine an amount of air volume exchange and at least one pulmonary health parameter as a function of the audio data, the image data, and the distance data; and
a display configured to present an indicator, the indicator representing the amount of air volume exchange.

9. The electronic device of claim 8, wherein the processor is further configured to:
determine an amount of effort put into the spirometry test by the user based on at least one of the audio data, the image data, and the distance data.

10. The electronic device of claim 8, wherein the at least one pulmonary health parameter comprises at least one of: peak expiratory flow (PEF), forced expiratory volume (FEV), FEV in one second (FEV1), forced vital capacity (FVC), forced expiratory flow (FEF), or forced inspiratory flow (FIF).

11. The electronic device of claim 8, wherein the processor is further configured to:
validate whether the user performed the spirometry test correctly; and
control the electronic device to provide real time feedback after validating that the user did not perform the spirometry test correctly.

12. The electronic device of claim 11, wherein the real time feedback indicates at least one mistake performed by the user during the spirometry test, the at least one mistake comprising at least one of: early termination of the spirometry test, an amount of effort by the user during the spirometry test being less than a baseline amount, inconsistent air flow by the user, or an air volume mismatch by the user.

13. The electronic device of claim 11, wherein the real time feedback comprises an instruction to the user to perform the spirometry test again.

14. The electronic device of claim 11, wherein the processor is further configured to:
provide second real time feedback during the spirometry test, the second real time feedback comprising at least one instruction to the user to adjust a behavior during the spirometry test.

15. A non-transitory computer readable medium containing computer readable program code that, when executed, causes at least one processor of an electronic device to:
concurrently receive, during a spirometry test of a user while the user inhales and exhales during the spirometry test, (i) audio data of the user from at least one audio sensor of the electronic device, (ii) image data of a mouth of the user from at least one image sensor of the electronic device, and (iii) distance data from at least one proximity sensor of the electronic device, the distance data indicating a distance from the mouth of the user to the electronic device;
determine an amount of air volume exchange and at least one pulmonary health parameter as a function of the audio data, the image data, and the distance data; and
present an indicator on a display of the electronic device, the indicator representing the amount of air volume exchange.

16. The non-transitory computer readable medium of claim 15, wherein the computer readable program code, when executed, further causes the at least one processor to:
determine an amount of effort put into the spirometry test by the user based on at least one of the audio data, the image data, and the distance data.

17. The non-transitory computer readable medium of claim 15, wherein the at least one pulmonary health parameter comprises at least one of: peak expiratory flow (PEF), forced expiratory volume (FEV), FEV in one second (FEV1), forced vital capacity (FVC), forced expiratory flow (FEF), or forced inspiratory flow (FIF).

18. The non-transitory computer readable medium of claim 15, wherein the computer readable program code, when executed, further causes the at least one processor to:
validate whether the user performed the spirometry test correctly; and
provide real time feedback after validating that the user did not perform the spirometry test correctly.

19. The non-transitory computer readable medium of claim 18, wherein the real time feedback indicates at least one mistake performed by the user during the spirometry test, the at least one mistake comprising at least one of: early termination of the spirometry test, an amount of effort by the user during the spirometry test being less than a baseline amount, inconsistent air flow by the user, or an air volume mismatch by the user.

20. The non-transitory computer readable medium of claim 18, wherein the real time feedback comprises an instruction to the user to perform the spirometry test again.

* * * * *